United States Patent [19]

Schneider

[11] Patent Number: 5,531,227

[45] Date of Patent: Jul. 2, 1996

[54] IMAGING DEVICE AND METHOD

[75] Inventor: M. Bret Schneider, Palo Alto, Calif.

[73] Assignee: Schneider Medical Technologies, Inc., Palo Alto, Calif.

[21] Appl. No.: 188,189

[22] Filed: Jan. 28, 1994

[51] Int. Cl.$^6$ ..................................................... A61B 5/00
[52] U.S. Cl. ......................................................... 128/653.1
[58] Field of Search ............................ 128/653.1, 653.2; 606/130; 364/413.13, 413.14, 413.2, 413.22

[56] References Cited

U.S. PATENT DOCUMENTS

| | | | |
|---|---|---|---|
| 4,791,934 | 12/1988 | Brunnett. | |
| 5,099,846 | 3/1992 | Hardy | 128/653.2 |
| 5,261,404 | 11/1993 | Mick et al. | 128/653.1 |
| 5,291,889 | 3/1994 | Kenet et al.. | |

OTHER PUBLICATIONS

Product brochure for DynaSight Sensor, Origin Instruments, 854 Greenview Drive, Grand Prairie, Texas 75050–2438 (2 pp. total).

Guthrie, B. L. and Adler, J. R., Jr., "Computer–Assisted Preoperative Planning, Interactive Surgery, and Frameless Stereotaxy" *Clinical Neurosurgery* (1992) 38:112–131.

Lavallèe, S. et al., "Matching 3-D Smooth Surfaces with their 2-D Projections using 3-D Distance Maps" *SPIE Geometric Methods in Computer Vision* (1991) 1570:322–336.

Levin, D. N. et al., "The Brain: Integrated Three–dimensional Display of MR and PET Images" *Radiology* (1989) 172(3):783–789.

Lorensen, W. et al., "Enhancing reality in the Operating Room" *Proceedings, Visualization '93, Oct. 25–29, 1993*, San Jose, CA, IEEE Computer Press, Los Alamos, CA (1993) pp. 410–415.

Pelizzari C. A. et al., "Accurate Three–Dimensional Registration of CT, PET, and/or MR Images of the Brain" *Journal of Computer Assisted Tomography* (1989) 13(1):20–26.

Wellls, W. et al., "Video Registration using Fiducials for Surgical Enhanced Reality" *Proceedings of the Annual International Conference of the IEEE Engineering in Medicine and Biology Society, Oct. 28–31, 1993*, San Diego, CA (1993) vol. 15, pp. 24–25.

Asarbayejani, A., et al., "Visually Controlled Graphics" *IEEE Transactions on Pattern Analysis and Machine Intelligence* (New York: IEEE, Inc., 1993) vol. 15, pp. 602–605.

Benabid, A. L., et al., "Computer–driven Robot for Stereotactic Neurosurgery," (in Kelly, P. J., et al., *Computers in Stereotactic Neurosurgery* (Boston: Blackwell Scientific Publications, 1992)) pp. 330–342.

Bezdek, J. C., et al., *Fuzzy Models for Pattern Recognition* (New York: IEEE, Inc., 1992) pp. 1–27.

(List continued on next page.)

*Primary Examiner*—Krista M. Zele
*Attorney, Agent, or Firm*—Morrison & Foerster

[57] ABSTRACT

A method and apparatus for obtaining and displaying in real time an image of an object obtained by one modality such that the image corresponds to a line of view established by another modality. In a preferred embodiment, the method comprises the following steps: obtaining a follow image library of the object via a first imaging modality; providing a lead image library obtained via the second imaging modality; referencing the lead image library to the follow image library; obtaining a lead image of the object in real time via the second imaging modality along a lead view; comparing the real time lead image to lead images in the lead image library via digital image analysis to identify a follow image line of view corresponding to the real time lead view; transforming the identified follow image to correspond to the scale, rotation and position of the lead image; and displaying the transformed follow image, the comparing, transforming and displaying steps being performed substantially simultaneously with the step of obtaining the lead image in real time.

32 Claims, 3 Drawing Sheets

OTHER PUBLICATIONS

Bhatia, G., et al., "Fiducial Point Localization in Multisensor 3D Surface Scanning" *SPIE vol. 1660 Biomedical Image Processing and Three–Dimensional Microscopy* (1992) pp. 375–386.

Burger, P., et al.,*Interactive Computer Graphics* (Menlo Park, California: Addison–Wesley Publishing Co., 1989) pp. 173–186; 195–235.

Chen, Sei–Wang, et al., "Strategies of Multi–view and Multi–matching for 3D Object Recognition" *CVGIP: Image Understanding* (1993) 57(1):121–130.

Chinzei, K., et al., "Quantitative Integration of Multimodality Medical Images" *SPIE Visualization in Biomedical Computing* (1992) 1808:187–195.

Darrell, T., et al., "Space Time Gestures," *Proceedings of the IEEE Computer Society Conferance on Computer Vision and Pattern Recognition, Jun. 15–18, 1993* (New York: IEEE, Inc., 1993) pp. 335–340.

Davies, E. R., *Machine Vision: Theory, Algorithms, Practicalities* (Academic Press, 1992) pp. 345–368; 369–410; 435–451.

Faugeras, Oliver, *Three–Dimensional Computer Vision, A Geometric Viewpoint* (Cambridge: MIT Press, 1989) pp. 245–300; 483–558.

Goerss, S. J., "An Interactive Stereotactic Operating Suite," (in Kelly, P. J., et al. *Computers in Stereotactic Neurosurgery* (Boston: Blackwell Scientific Publications, 1992)) pp. 67–86.

Haralick, R. M., et al., *Computer and Robot Vision*, vol. 2. (Menlo Park, California: Addison–Wesley Publishing Co., 1993) pp. 43–185; 187–288; 289–378; 493–533.

Heilbrun, M. P., "The Evolution and Integration of Microcomputers Used with the Brown–Roberts–Wells (BRW) Image–guided Stereotactic System," (in Kelly, P. J., et al. *Computers in Stereotactic Neurosurgery* (Boston: Blackwell Scientific Publications, 1992)) pp. 43–55.

Hunton, N. K., "Wandering Through the Brain," *Computer Graphics World* (Oct. 1992) pp. 71–72.

Jain, A. K., "Image Analysis and Computer Vision," *Fundamentals of Digital Image Processing* (Englewood Cliffs, NJ: Prentice–Hall, Inc., 1989) pp. 342–430.

Jiang, H., et al., "A New Approach to 3–D Registration of Multimodality Medical Images by Surface Matching" *SPIE, Visualization in Biomedical Computing* (1992) 1808:196–213.

Kalawasky, R., *The Science of Virtual Reality and Virtual Environments: A Technical, Scientific and Engineering Reference on Virtual Environments* (Menlo Park, California: Addison–Wesley Publishing Co., 1993) pp. 315–318.

Kall, B. A., "Comprehensive Multimodality Surgical Planning and Interactive Neurosurgery," (in Kelly, P. J., et al. *Computers in Stereotactic Neurosurgery* (Boston: Blackwell Scientific Publications 1992)) pp. 209–229.

Kelly, P. J. (in Kelly, P. J., et al. *Computers in Stereotactic Neurosurgery* (Boston: Blackwell Scientific Publications 1992) pp. 352–353, 354–355.

Kelly, P. J. "Quantitative Virtual Reality Surgical Simulation, Minimally Invasive Stereotactic Neurosurgery and Frameless Stereotactic Technologies," Proceedings from Medicine Meets Virtual Reality II–Interactive Technology & Healthcare: Visionary Applications for Simulation, Visualization, Robotics, Jan. 27–30, 1994, San Diego, California, pp. 104–108.

Koch, R. "Dynamic 3–D Scene Analysis through Synthesis Feedback Control" *IEEE Transactions on Pattern Analyis and Machine Intelligence* (New York: IEEE, Inc., 1993) 15(6):556–568.

Krueger, M. W., "the Emperor's New Realities," *Virtual Reality World* (Nov./Dec. 1993) pp. 18–33.

Lewis, R. *Practical Digital Image Processing*, (New York: Ellis Horwood Limited, 1990) pp. 211–217.

Moshell, J. M., "A Survey of Virtual Environments: Research in North America" *Virtual Reality World* (Jan./Feb. 1994) pp. 24–36.

[no author] *On The Cutting Edge of Technology* (Sams Publishing, 1993) pp. 2–14.

Peters, T. M., et al., (in Kelly, P. J., et al. *Computers in Stereotactic Neurosurgery* (Boston: Blackwell Scientific Publications, 1992)) pp. 196–197.

Pratt, W. K., *digital Image Processing* (New York: John Wiley & Sons, Inc. 1991) p. 636–671.

Product brochure for: Cognex 4400 Machine Vision System and Cognex Software Overview, (8 pages total), Cognex Corporation, 15 Crawford Street, Needham, MA 02194.

Roberts, D. W., et al., "Computer Image Display During Frameless Stereotactic Surgery," (in Kelly, P. J., et al. *Computers in Stereotactic Neurosurgery* (Boston: Blackwell Scientific Publications, 1992)) pp. 313–319.

Rosenfeld, A., "The Fuzzy Geometry of Image Subsets," (in Bezdek, J. C. et al., *Fuzzy Models for Pattern Recognition* (New York: IEEE, Inc., 1992)) pp. 340–346.

Russ, J. C., *The Image Processing Handbook* pp. 375–433 (Boca Raton: CRC Press, 1992).

[no author] "Symmetric Multiprocessing Systems Technical Report" (56 pp. total) SilconGraphics, Computer Systems, Mountain View, California, 1993.

Siy, P., et al., "Fuzzy Logic for Handwritten Numeral Character Recognition," (in Bezdek, J. C., et al., *Fuzzy Models for Pattern Recognition* (New York: IEEE, Inc., 1992)) pp. 321–325.

Stone, R. J., "A Year in the Life of British Virtual Reatity," *Virtual Reality World* (Jan./Feb. 1994) pp.49–62.

Suetens, P., et al. (in Kelly, P. J., et al. *Computers in Stereotactic Neurosurgery* (Boston: Blackwell Scientific Publications, 1992) pp. 252–253.

van den Elsen, P. A., et al., "Image Fusion Using Geometrical Features" *SPIE, Visualization in Biomedical Computing* (1992) 1808:172–186.

Young, R. F., et al., "Robot–aided Surgery" (in Kelly, P. J., et al., *Computers in Stereotactic Neurosurgery* (Boston: Blackwell Scientific Publications, 1992)) pp. 320–329.

Adler, J. R., "Image–Based Frameless Stereotactic Radiosurgery" (in Maciunas, R. J., ed., *Interactive Image–Guided Neurosurgery* (American Association of Neurological Surgeons, 1993)), pp. 81–89.

Heilbrun, M. P. et al., "Implementation of a Machine Vision Method for Stereotactic Localization and Guidance" (in Maciunas, R. J., ed., *Interactive Image–Guided Neurosurgery* (American Association of Neurological Surgeons, 1993)), pp. 169–177.

Winston, P. H., *Artificial Intelligence* (Menlo Park, CA: Addison–Wesley Publishing Co., 1992) pp. 531–551.

"The Future of Medicine" *The Economist* (Mar. 19, 1984).

IMAGING DEVICE AND METHOD

TECHNICAL FIELD

This invention relates generally to an imaging device and method and, in particular, to a medical imaging device and method.

BACKGROUND OF THE INVENTION

While invasive surgery may have many beneficial effects, it can cause physical and psychological trauma to the patient from which recovery is difficult. A variety of minimally invasive surgical procedures are therefore being developed to minimize trauma to the patient. However, these procedures often require physicians to perform delicate procedures within a patient's body without being able to directly see the area of the patient's body on which they are working. It has therefore become necessary to develop imaging techniques to provide the medical practitioner with information about the interior of the patient's body.

Additionally, a non-surgical or pre-surgical medical evaluation of a patient frequently requires the difficult task of evaluating imaging from several different modalities along with a physical examination. This requires mental integration of numerous data sets from the separate imaging modalities, which are seen only at separate times by the physician.

A number of imaging techniques are commonly used today to gather two-, three- and four-dimensional data. These techniques include ultrasound, computerized X-ray tomography (CT), magnetic resonance imaging (MRI), electric potential tomography (EPT), positron emission tomography (PET), brain electrical activity mapping (BEAM), magnetic resonance angiography (MRA), single photon emission computed tomography (SPECT), magnetoelectroencephalography (MEG), arterial contrast injection angiography, digital subtraction angiography and fluoroscopy. Each technique has attributes that make it more or less useful for creating certain kinds of images, for imaging a particular part of the patient's body, for demonstrating certain kinds of activity in those body parts and for aiding the surgeon in certain procedures. For example, MRI can be used to generate a three-dimensional representation of a patient's body at a chosen location. Because of the physical nature of the MRI imaging apparatus and the time that it takes to acquire certain kinds of images, however, it cannot conveniently be used in real time during a surgical procedure to show changes in the patient's body or to show the location of surgical instruments that have been placed in the body. Ultrasound images, on the other hand, may be generated in real time using a relatively small probe. The image generated, however, lacks the accuracy and three-dimensional detail provided by other imaging techniques.

Medical imaging systems that utilize multi-modality images and/or position-indicating instruments are known in the prior art. Hunton, N., *Computer Graphics World* (October 1992, pp. 71–72) describes a system that uses an ultrasonic position-indicating probe to reference MRI or CT images to locations on a patient's head. Three or four markers are attached to the patient's scalp prior to the MRI and/or CT scans. The resulting images of the patient's skull and brain and of the markers are stored in a computer's memory. Later, in the operating room, the surgeon calibrates a sonic probe with respect to the markers (and, therefore, with respect to the MRI or CT image) by touching the probe to each of the markers and generating a sonic signal which is picked by four microphones on the operating table. The timing of the signals received by each microphone provides probe position information to the computer. Information regarding probe position for each marker registers the probe with the MRI and/or CT image in the computer's memory. The probe can thereafter be inserted into the patient's brain. Sonic signals from the probe to the four microphones will show how the probe has moved within the MRI image of the patient's brain. The surgeon can use information of the probe's position to place other medical instruments at desired locations in the patient's brain. Since the probe is spacially located with respect to the operating table, one requirement of this system is that the patient's head be kept in the same position with respect to the operating table as well. Movement of the patient's head would require a recalibration of the sonic probe with the markers.

Kalawasky, R., "The Science of Virtual Reality and Virtual Environments," pp. 315–318 (Addison-Wesley 1993), describes an imaging system that uses a position sensing articulated arm integrated with a three-dimensional image processing system such as a CT scan device to provide three-dimensional information about a patient's skull and brain. As in the device described by Hunton, metallic markers are placed on the patient's scalp prior to the CT scan. A computer develops a three-dimensional image of the patient's skull (including the markers) by taking a series of "slices" or planar images at progressive locations, as is common for CT imaging, then interpolating between the slices to build the three-dimensional image. After obtaining the three-dimensional image, the articulated arm can be calibrated by correlating the marker locations with the spacial position of the arm. So long as the patient's head has not moved since the CT scan, the arm position on the exterior of the patient can be registered with the three-dimensional CT image.

Heilbrun, M. P., "The Evolution and Integration of Microcomputers Used with the Brown-Roberts-Wells (BRW) Image-guided Stereotactic System," (in Kelly, P. J., et al. "Computers in Stereotactic Neurosurgery," pp. 43–55 (Blackwell Scientific Publications 1992)) briefly mentions the future possibility of referencing (within the same image set) intracranial structures to external landmarks such as a nose. However, he does not describe how this would be accomplished, nor does he describe such a use for multi-modality image comparison or compositing.

Peters, T. M., et al., (in Kelly, P. J., et al. "Computers in Stereotactic Neurosurgery," p. 196 (Blackwell Scientific Publications 1992)) describe the use of a stereotactic frame with a system for using image analysis to read position markers on each tomographic slice taken by MR or CT, as indicated by the positions of cross-sections of N-shaped markers on the stereotactic frame. While this method is useful for registering previously acquired tomographic data, it does not help to register a surgeon's view to that data. Furthermore, the technique cannot be used without a stereotactic frame.

Goerss, S. J., "An Interactive Stereotactic Operating Suite," and Kall, B. A., "Comprehensive Multimodality Surgical Planning and Interactive Neurosurgery," (both in Kelly, P. J., et al. "Computers in Stereotactic Neurosurgery," pp. 67–86, 209–229 (Blackwell Scientific Publications 1992)) describe the Compass™ system of hardware and software. The system is capable of performing a wide variety of image processing functions including the automatic reading of stereotactic frame fiducial markers, three-dimensional reconstructions from two-dimensional data, and image transformations (scaling, rotating, translating).

The system includes an "intramicroscope" through which computer-generated slices of a three-dimensionally reconstructed tumor correlated in location and scale to the surgical trajectory can be seen together with the intramicroscope's magnified view of underlying tissue. Registration of the images is not accomplished by image analysis, however. Furthermore, there is no mention of any means by which a surgeon's instantaneous point of view is followed by appropriate changes in the tomographic display. This method is also dependent upon a stereotactic frame, and any movement of the patient's head would presumably disable the method.

Suetens, P., et al. (in Kelly, P. J., et al. "Computers in Stereotactic Neurosurgery," pp. 252–253 (Blackwell Scientific Publications 1992)) describe the use of a head mounted display with magnetic head trackers that changes the view of a computerized image of a brain with respect to the user's head movements. The system does not, however, provide any means by which information acquired in real time during a surgical procedure can be correlated with previously acquired imaging data.

Roberts, D. W., et al., "Computer Image Display During Frameless Stereotactic Surgery," (in Kelly, P. J., et al. "Computers in Stereotactic Neurosurgery," pp. 313–319 (Blackwell Scientific Publications 1992)) describe a system that registers pre-procedure images from CT, MRI and angiographic sources to the actual location of the patient in an operating room through the use of an ultrasonic rangefinder, an array of ultrasonic microphones positioned over the patient, and a plurality of fiducial markers attached to the patient. Ultrasonic "spark gaps" are attached to a surgical microscope so that the position of the surgical microscope with respect to the patient can be determined. Stored MRI, CT and/or angiographic images corresponding to the microscope's focal plane may be displayed.

Kelly, P. J. (in Kelly, P. J., et al. "Computers in Stereotactic Neurosurgery," p. 352 (Blackwell Scientific Publications 1992)) speculates about the future possibility of using magnetic head tracking devices to cause the surgical microscope to follow the surgeon's changing field of view by following the movement within the established three-dimensional coordinate system. Insufficient information is given to build such a system, however. Furthermore, this method would also be stereotactic frame dependent, and any movement of the patient's head would disable the coordinate correlation.

Krueger, M. W., "The Emperor's New Realities," pp. 18–33, *Virtual Reality World* (Nov./Dec. 1993) describes generally a system which correlates real time images with stored images. The correlated images, however, are of different objects, and the user's point of view is not tracked.

Finally, Stone, R. J., "A Year in the Life of British Virtual Reality", p. 49–61, *Virtual Reality World* (Jan./Feb. 1994) discusses the progress of Advanced Robotics Research Limited in developing a system for scanning rooms with a laser rangefinder and processing the data into simple geometric shapes "suitable for matching with a library of a priori computer-aided design model primitives." While this method seems to indicate that the group is working toward generally relating two sets of images acquired by different modalities, the article provides no means by which such matching would be accomplished. Nor does there seem to be classification involved at any point. No means are provided for acquiring, processing, and interacting with image sets in real time, and no means are provided for tracking the instantaneous point of view of a user who is performing a procedure, thereby accessing another data set.

As can be appreciated from the prior art, it would be desirable to have an imaging system capable of displaying single modality or multimodality imaging data, in multiple dimensions, in its proper size, rotation, orientation, and position, registered to the instantaneous point of view of a physician examining a patient or performing a procedure on a patient. Furthermore, it would be desirable to do so without the expense, discomfort, and burden of affixing a stereotactic frame to the patient in order to accomplish these goals. It would also be desirable to utilize such technology for non-medical procedures such as the repair of a device contained within a sealed chassis.

SUMMARY OF THE INVENTION

This invention provides a method and apparatus for obtaining and displaying in real time an image of an object obtained by one modality such that the image corresponds to a line of view established by another modality. In a preferred embodiment, the method comprises the following steps: obtaining a follow image library of the object via a first imaging modality; providing a lead image library obtained via the second imaging modality; referencing the lead image library to the follow image library; obtaining a lead image of the object in real time via the second imaging modality along a lead view; comparing the real time lead image to lead images in the lead image library via digital image analysis to identify a follow image line of view corresponding to the lead view; transforming the identified follow image to correspond to the scale, rotation and position of the lead image; and displaying the transformed follow image, the comparing, transforming and displaying steps being performed substantially simultaneously with the step of obtaining the lead image in real time.

The invention is described in further detail below with reference to the drawings.

DETAILED DESCRIPTION OF THE INVENTION

Definitions

Figure 1:
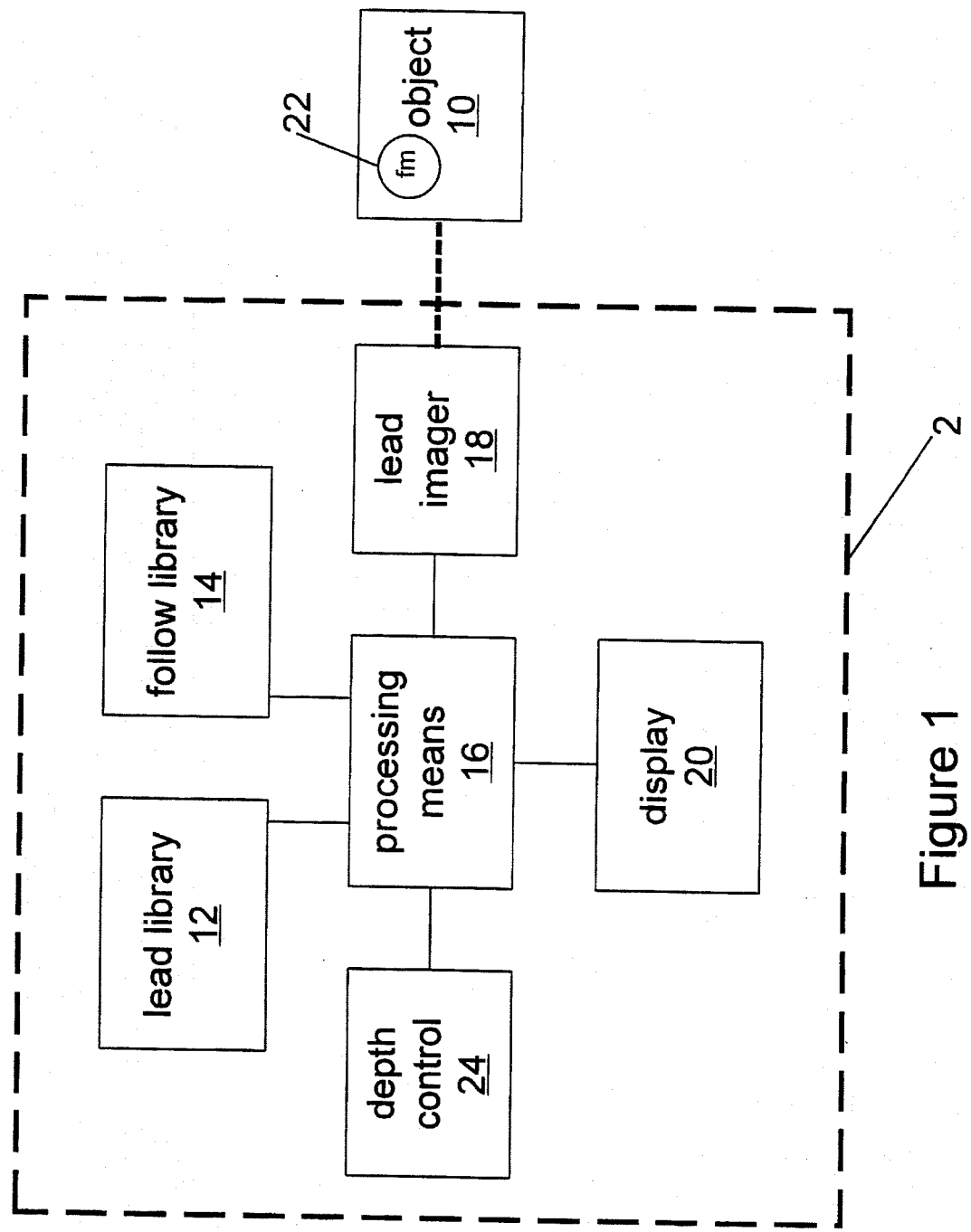
FIG. 1 is a block diagram showing a preferred embodiment of the imaging device of this invention.

The following definitions are useful in understanding and using the device and method of the invention.

Image. As used herein "image" means the data that represents the spacial layout of anatomical or functional features of a patient, which may or may not be actually represented in visible, graphical form. In other words, image data sitting in a computer memory, as well as an image appearing on a computer screen, will be referred to as an image or images. Non-limiting examples of images include an MRI image, an angiography image, and the like. When using a video camera as a data acquisition method, an "image" refers to one particular "frame" in the series that is appropriate for processing at that time. Because the ability to "re-slice" a three-dimensional reconstruction of a patient's body in a plane corresponding to the trajectory of the "lead view" (typically the line of view from which the surgeon wishes to view the procedure) is important to this method, the "image" may refer to an appropriately re-sliced image of a three-dimensional image reconstruction, rather than one of the originally acquired two-dimensional files from which the reconstructions may have been obtained. The term image is also used to means any portion of an image that has been selected, such as a fiducial marker, subobject, or knowledge representation.

Imaging modality. As used herein "imaging modality" means the method or mechanism by which an image is obtained, e.g., MRI, CT, video, ultrasound, etc.

Lead view. As used herein "lead view" means the line of view toward the object at any given time. Typically the lead view is the line of view through which the physician at any given time wishes to view the procedure. In the case where a see-through head-mounted display and head-mounted camera are utilized, this should be the instantaneous line of view of the physician. As the lead view shifts, all other images must adjust their views to that of the lead view in order to make all of the images that converge to make a resulting composite image accurate.

Lead image. As used herein "lead image" is an image obtained through the same modality as the lead view. For example, if the lead view is the physician's view of the surface of the patient, the lead image could be a corresponding video image of the surface of the patient.

Follow image. As used herein "follow image" will be an image which must be transformed and possibly sliced to the specifications of the lead view and slice depth control. A properly sliced and transformed follow image will usually be in a plane parallel with that of the lead image, and consequently, orthogonal to the lead view, although other slice contours could be used. A properly transformed follow image will be at the same angle of the view as the lead image, but at a depth to be separately determined.

Composite image. As used herein "composite image" is the image that results from the combination of properly registered lead and follow images from two or more sources, each source representing a different modality.

Fiducial marker. As used herein "fiducial marker" means a feature, image structure, or subobject present in lead or follow images that can be used for image analysis, matching, coordinate interreferencing or registration of the images and creation of a composite image.

Feature extraction. As used herein "feature extraction" means a method of identification of image components which are important to the image analysis being conducted. These may include boundaries, angles, area, center of mass, central moments, circularity, rectangularity and regional gray-scale intensities in the image being analyzed.

Segmentation. As used herein "segmentation" is the method of dividing an image into areas which have some physical significance in terms of the original scene that the image attempts to portray. For example, segmentation may include the demarcation of a distinct anatomical structure, such as an external auditory meatus, although it may not be actually identified as such until classification. Thus, feature extraction is one method by which an image can be segmented. Additionally, previously segmented areas may be subsequently subjected to feature extraction. Other non-limiting examples of methods of segmentation which are well known in the area of image analysis include: thresholding, edge detection, Hough transform, region growing, run-length connective analysis, boundary analysis, template matching and the like. See, e.g., Rosenfeld, A., "The fuzzy geometry of image subsets," (in Bezdek, J. C. et al., "Fuzzy Models for Pattern Recognition," pp. 340–346 (IEEE 1992)).

Classification. As used herein "classification" means a step in the imaging method of the invention in which an object is identified as being of a certain type, based on its features. For example, a certain segmented object in an image might be identified by a computer as being an external auditory meatus based on if it falls within predetermined criteria for size, shape, pixel density, and location relative to other segmented objects. In this invention, classification is extended to include the angle, or Cartesian location, from which the object is viewed ("line of view"), for example, an external auditory meatus viewed from 30° North and 2° West of a designated origin. A wide variety of classification techniques are known, including statistical techniques (see, e.g., Davies, E. R., "Machine Vision: Theory, Algorithms, Practicalities," pp. 435–451 (Academic Press 1992)) and fuzzy logic techniques (see, e.g., Bezdek, J. C., et al., "Fuzzy Models for Pattern Recognition," pp. 1–27 (IEEE 1992); Siy, P., et al., "Fuzzy Logic for Handwritten Numeral Character Recognition," (in Bezdek, J. C., et al., "Fuzzy Models for Pattern Recognition," pp. 321–325 (IEEE 1992)). Classification techniques are discussed in Faugeras, "Three-Dimensional Computer-Vision," pp. 483–558 (MIT Press 1989) and Haralick, R. M., et al., "Computer and Robot Vision," vol. 2, pp. 43–185, 289–378, 493–533 (Addison-Wesley 1993).

Transformation. As used herein, "transformation" means processing an image such that it is translated (moved in a translational fashion), rotated (in two or three dimensions), scaled, sheared, warped, placed in perspective or otherwise altered according to specified criteria. See Burger, P., "Interactive Computer Graphics," pp. 173–186 (Addison-Wesley 1989).

Registration. As used herein, "registration" means alignment process by which two images of like or corresponding geometries and of the same set of objects are positioned coincident with each other so that corresponding points of the imaged scene appear in the same position on the registered images.

Description of the Preferred Embodiments

For convenience, the preferred embodiment of the invention is discussed in the context of medical applications, such as in brain surgery or other invasive surgeries. The invention is also applicable to other uses, including but not limited to medical examinations, analysis of ancient and often fragile artifacts, airplane luggage, chemical compositions (in the case of nuclear magnetic resonance spectral analysis); the repair of closed pieces of machinery through small access ways; and the like.

The invention improves earlier methods and devices for creating multimodality composite images by providing a new way of selecting and registering the image data. The invention also improves upon earlier methods of image viewing by adjusting to the user's line of sight while in a dynamic field of view. FIG. 1 is a block diagram of an imaging system 2 for displaying an image of an object 10 according to a preferred embodiment of this invention. A lead library 12 and a follow library 14 of images of the object 10 obtained by two different modalities communicate with a processing means 16. The imaging modality of either library could be a CT scan, an MRI scan, a sonigram, an angiogram, video or any other imaging technique known in the art. Each library contains image data relating to the object.

Most preferably, at least one of the imaging devices is a device that can view and construct an image of the interior of object 10. The images (or data gleaned from their analysis) are stored within the libraries in an organized and retrievable manner. The libraries may be any suitable means of storing retrievable image data, such as, for example, electronic memory (RAM, ROM, etc.), magnetic memory (magnetic disks or tape), or optical memory (CD-ROM, WORM, etc.).

The processing means 16 interreferences corresponding images in image libraries 12 and 14 to provide a map or table relating images or data in one library to images or data in the other. The preferred interreferencing method is described in detail below. Processing means 16 may be a stand-alone computer such as a SGI RealityEngine (available from Silicon Graphics, Inc.) which has been loaded with suitable software. Alternatively, processing means 16 may be an image processor specially designed for this particular application.

A lead imager 18 is provided to obtain an image of object 10 along a chosen perspective or line of view. For example, if object 10 is a patient in an operating room, lead imager 10 may be a video camera that obtains video images of the patient along the line of sight of the attending physician, such as a head-mounted video camera. Lead imager 18 sends its lead image to processing means 16 which interreferences the lead image with a corresponding follow image from follow image library 14 and transforms the image to correspond to the lead image. The depth at which the follow image is sliced may be controlled by a depth control 24 (such as a mouse, joy stick, knob, or other means) to identify the depth at which the follow image slice should be taken. The follow image (or, alternatively, a composite image combining the lead image from lead imager 18 and the corresponding transformed follow image from library 14) may be displayed on display 20. Display 20 may be part of processing means 16 or it may be an independent display.

In the preferred embodiment, object 10 has at least one fiducial marker 22. The fiducial marker is either an inherent feature of object 10 (such as a particular bone structure within a patient's body) or a natural or artificial subobject attached to or otherwise associated with object 10. The system and methods of this invention use one or more fiducial markers to interreference the lead and follow images or to interreference lead images acquired in real time to lead images or data in the lead image library, as discussed in more detail below.

Figure 2:
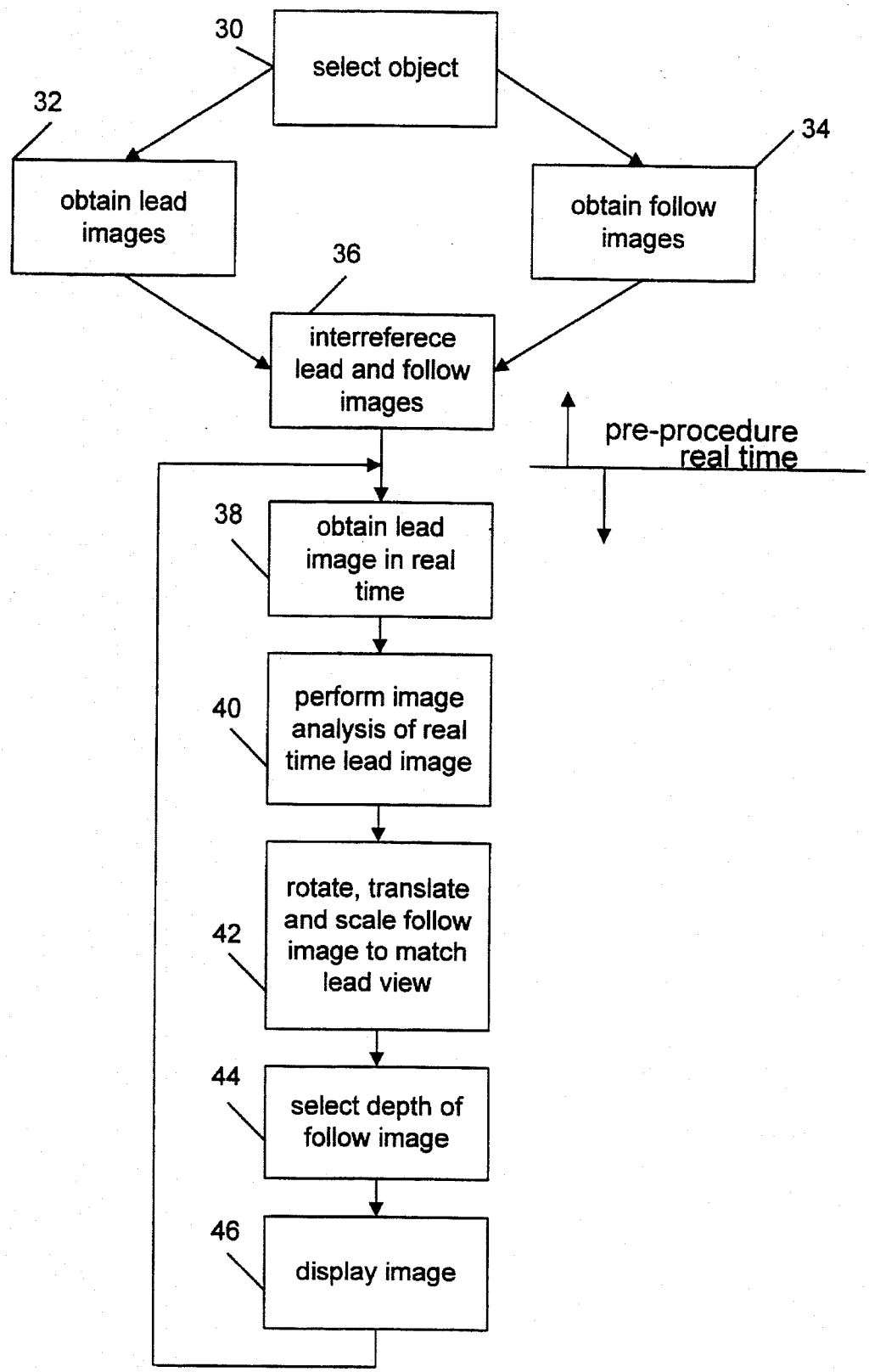
FIG. 2 is a flow chart illustrating a preferred embodiment of the method of this invention.

FIG. 2 is a flow chart showing the basic method of this invention. In the flowchart, steps are divided into those accomplished before the start of the surgical procedure, and those that are accomplished in real time, i.e., during the procedure. In this example, the object of interest is a body or a specific part of the body, such as a patient's head, and the two imaging modalities are an MRI scan of the patient's head (the follow image modality) and a video image of the surface of the patient's head (the lead image modality). It should be understood, however, that the invention could be used in a variety of environments and applications.

In the preferred embodiment, the lead and follow images are interreferenced prior to the surgical procedure to gather information for use in real time during the surgical procedure. Interreferencing of the lead and follow images gathered in this pre-procedure stage is preferably performed by maintaining common physical coordinates between the patient and the video camera and between the patient and the MRI device. The first step of this preferred method (indicated generally at block 30 of FIG. 2) therefore is to mount the patient's head immovably to a holder such as a stereotactic frame.

Next, to gather follow image information, an MRI scan of the patient's head and stereotactic frame is taken, and the three-dimensional data (including coordinate data relating to the patient's head and the stereotactic frame) are processed in a conventional manner and stored in memory, such as in a follow image library, as shown in block 34. The pre-process lead video images of the patient's head are preferably obtained via a camera that automatically obtains digital images at precise locations. Robotic devices built to move instruments automatically between precise stereotactic locations have been described by Young, R. F., et al., "Robot-aided Surgery" and Benabid, A. L., et al., "Computer-driven Robot for Stereotactic Neurosurgery," (in Kelly, P. J., et al., "Computers in Stereotactic Neurosurgery," pp. 320–329, 330–342 (Blackwell Scientific Publications, 1992)). Such devices could be used to move a camera to appropriate lead view angles for the acquisition of the lead library. For example, using the stereotactic frame, the video camera could move about the head in three planes, obtaining an image every 2 mm. Each image is stored in a lead image library along with information about the line of view or trajectory from which the image was taken. The stereotactic frame may be removed from the patient's head after all these images have been obtained.

Keeping the patient's head immovably attached to the stereotactic frame during the MRI and video image obtaining steps gives the lead (video) and follow (MRI) image data a common coordinate system. Thus, identification of a line of view showing a portion of a stored video image is equivalent to identification of the corresponding line of view in the stored MRI image. Information interreferencing the stored lead and follow images is itself stored for use for real time imaging during the surgical procedure.

As the final step in the pre-procedure part of the method, the video lead images are digitally analyzed to identify predefined fiducial markers. In the preferred embodiment, the digital representation of each lead image stored in the lead image library is segmented or broken down into subobjects. Segmentation can be achieved by any suitable means known in the art, such as by feature extraction, thresholding, edge detection, Hough transforms, region growing, run-length connectivity analysis, boundary analysis, template matching, etc. The preferred embodiment of this invention utilizes a Canny edge detection technique, as described in R. Lewis, "Practical Digital Image Processing" (Ellis Horwood, Ltd., 1990). The result of the segmentation process is the division of the video image into subobjects which have defined boundaries, shapes, and positions within the overall image.

The Canny edge detection segmenting technique can be modified depending on whether the image is in two or three dimensions. In this example the image is, of course, a two-dimensional video image. Most segmentation approaches can be adapted for use with either two-dimensional or three-dimensional images, although most written literature concerns two-dimensional image segmentation. One method by which a two-dimensional approach can be adapted for the segmentation of a three-dimensional object is to run the two-dimensional segmentation program on each two-dimensional slice of the series that represents the three-dimensional structure. Subsequent interpolation of each corresponding part of the slices will result in a three-dimensional image containing three-dimensional segmented objects.

To help resolve the difficulties in segmenting low-contrast points in images (particularly medical images), much effort in the field is being devoted to the development of new segmentation techniques. Particularly likely to be useful in the future are those statistical segmentation techniques that assign to each point a certain degree of probability as to whether or not it is a part of a given segmented object. That probability is based upon a variety of factors including pixel intensity and location with respect to other pixels of given qualities. Once probabilities of each pixel have been determined, assessments can be made of the pixels as a group, and segmentation can be achieved with improved accuracy. Using such techniques, segmentation of a unified three-dimensional file is preferable to performing a segmentation on a series of two-dimensional images, then combining them, since the three-dimensional file provides more points of reference when making a statistic-based segmentation decision. Fuzzy logic techniques may also be used, such as those described by Rosenfeld, A., "The fuzzy geometry of image subsets," (in Bezdek, J. C., et al., "Fuzzy Models for Pattern Recognition," pp. 340–346 (IEEE Press 1991)).

The final part of this image analysis step is to classify the subobjects. Classification is accomplished by means well known in the art. A wide variety of image classification methods are described in a robust literature, including those based on statistical, fuzzy, relational, and feature-based models. Using a feature-based model, feature extraction is performed on a segmented or unsegmented image. If there is a match between the qualities of the features and those qualities previously assigned in the class definition, the object is classified as being of that type. Class types can describe distinct anatomic structures, and in the case of this invention, distinct anatomic structures as they appear from distinct points of view.

In general, the features of each segmented area of an image are compared with a list of feature criteria that describe a fiducial marker. The fiducial marker is preferably a unique and identifiable feature of the object, such as surface shapes caused by particular bone or cartilage structures within the patient's body. For example, the system could use an eyeball as a fiducial marker by describing it as a roughly spherical object having a diameter within a certain range of diameters and a pixel intensity within a certain range of intensities. Alternatively, the fiducial marker can be added to the object prior to imaging solely for the purpose of providing a unique marker, such as a marker on the scalp. Such a marker would typically be selected to be visible in each imaging modality used. For example, copper sulfate capsules are visible both to MRI and to a video camera. As yet another alternative, the stereotactic frame used in the pre-procedure steps may be left attached to the head. In any case, if an object can be automatically recognized, it can be classified as a fiducial marker.

The segmentation, feature extraction and classification steps utilized by this invention may be performed with custom software. Suitable analysis of two-dimensional images may be done with commercially available software such as Global Lab Image, with processing guided by a macro script.

After the images stored in the lead and follow libraries have been interreferenced, and the fiducial markers in the lead images have been identified, the system is ready for use in real time imaging during a medical procedure. In this example, real time lead images of the patient's head along the physician's line of sight are obtained through a digital video camera mounted on the physician's head, as in block 38 of FIG. 2. Individual video images are obtained via a framegrabber.

In the preferred embodiment, each video image is correlated in real time with a corresponding image in the lead image library, preferably using the digital image analysis techniques discussed above. Specifically, the lead image is segmented, and the subobjects in the segmented lead image are classified to identify one or more fiducial markers. Each fiducial marker in the real time lead image is matched in position, orientation and size with a corresponding fiducial marker in the lead image library and, thus, to a corresponding position orientation and size in the follow image library via the interreferencing information. The follow image is subsequently translated, rotated in three dimensions, and scaled to match the specifications of the selected lead view. The process of translating and/or rotating and/or scaling the images to match each other is known as transformation.

Because the follow image in this example is three-dimensional, this matching step yields a three-dimensional volume, only the "surface" of which would ordinarily be visible. The next step in the method is therefore to select the desired depth of the slice one wishes to view. The depth of slice may be selected via a mouse, knob, joystick or other control mechanism. The transformed follow image is then sliced to the designated depth by means known in the art, such as described in Russ, J. C., "The Image Processing Handbook," pp. 393–400 (CRC Press 1992); Burger, P., et al., "Interactive Computer Graphics," pp. 195–235 (Addison-Wesley 1989).

In general, slicing algorithms involve designating a plane of slice in the three-dimensional image and instructing the computer to ignore or to make transparent any data located between the viewer and that plane. Because images are generally represented in memory as arrays, and because the location of each element in the array is mathematically related to the physical space that it represents, a plane of cut can be designated by mathematically identifying those elements of the array that are divided by the plane. The resulting image is a two-dimensional representation of the view into the three-dimensional object sliced at the designated plane.

The system can display the sliced follow image alone, or as a composite image together with a corresponding lead image, such as by digital addition of the two images. Additionally, the transformed and sliced follow image can be projected onto a see-through display mounted in front of the physician's eyes so that it is effectively combined with the physician's direct view of the patient. Alternatively, the composite lead and follow images can be displayed on a screen adjacent the patient. The displayed images remain on the screen while a new updated lead image is obtained, and the process starts again.

The imaging system performs the steps of obtaining the lead image and display of the corresponding follow or composite image substantially in real time. In other words, the time lag between obtaining the lead image and display of the follow or composite image is short enough that the displayed image tracks changes of the lead view substantially in real time. Thus, in the medical context, new images will be processed and displayed at a frequency that enables the physician to receive a steady stream of visual feedback reflecting the movement of the physician, the patient, medical instruments, etc.

In a first alternative embodiment, interreferencing of the images in the lead and follow libraries in the pre-procedure portion of the imaging method is done solely by digital image analysis techniques. Each digitized lead image (for example, a video image) is segmented, and the subobjects are classified to identify fiducial markers. Fiducial markers in the follow images (e.g., surface views of MRI images) are also identified in the same way. A map or table interreferencing the lead and follow images is created by transforming the follow image fiducial markers to correspond to the lead image fiducial markers. The interreferencing information is stored for use during the real time imaging process. Alternatively, pattern matching techniques may be used to match the images without identifying specific fiducial markers. Davies, E. R., "Machine Vision: Theory, Algorithms, Practicalities," pp. 345–368 (Academic Press 1992); Haralick, R. M., et al., "Computer and Robot Vision," vol. 2, pp. 289–378, 493–533 (Addison-Wesley 1993); Siy, P., et al., "Fuzzy Logic for Handwritten Numeral Character Recognition," in Bezdek, J. C., et al., "Fuzzy Models for Pattern Recognition," pp. 321–325 (IEEE 1992)).

After obtaining the lead and follow image libraries and interreferencing the lead and follow images in the libraries, the method of the first alternative embodiment may then be used to display appropriate slices of the follow images that correspond to lead images obtained in real time. Thus, for example, real time video images of a patient obtained by a video camera mounted on a physician's head can be correlated with lead images in the lead image library via the digital image analysis techniques described above with respect to the preferred embodiment. The stored interreferencing information can then be used to identify the follow image corresponding to the real time lead image.

The follow image is transformed to match the size, location and orientation of the lead image. The three-dimensional follow image is also sliced to a depth selected via a depth control. The transformed and sliced follow image is then displayed alone or as a composite image together with the real time video image. The process repeats when a subsequent real time video image is obtained.

Figure 3:
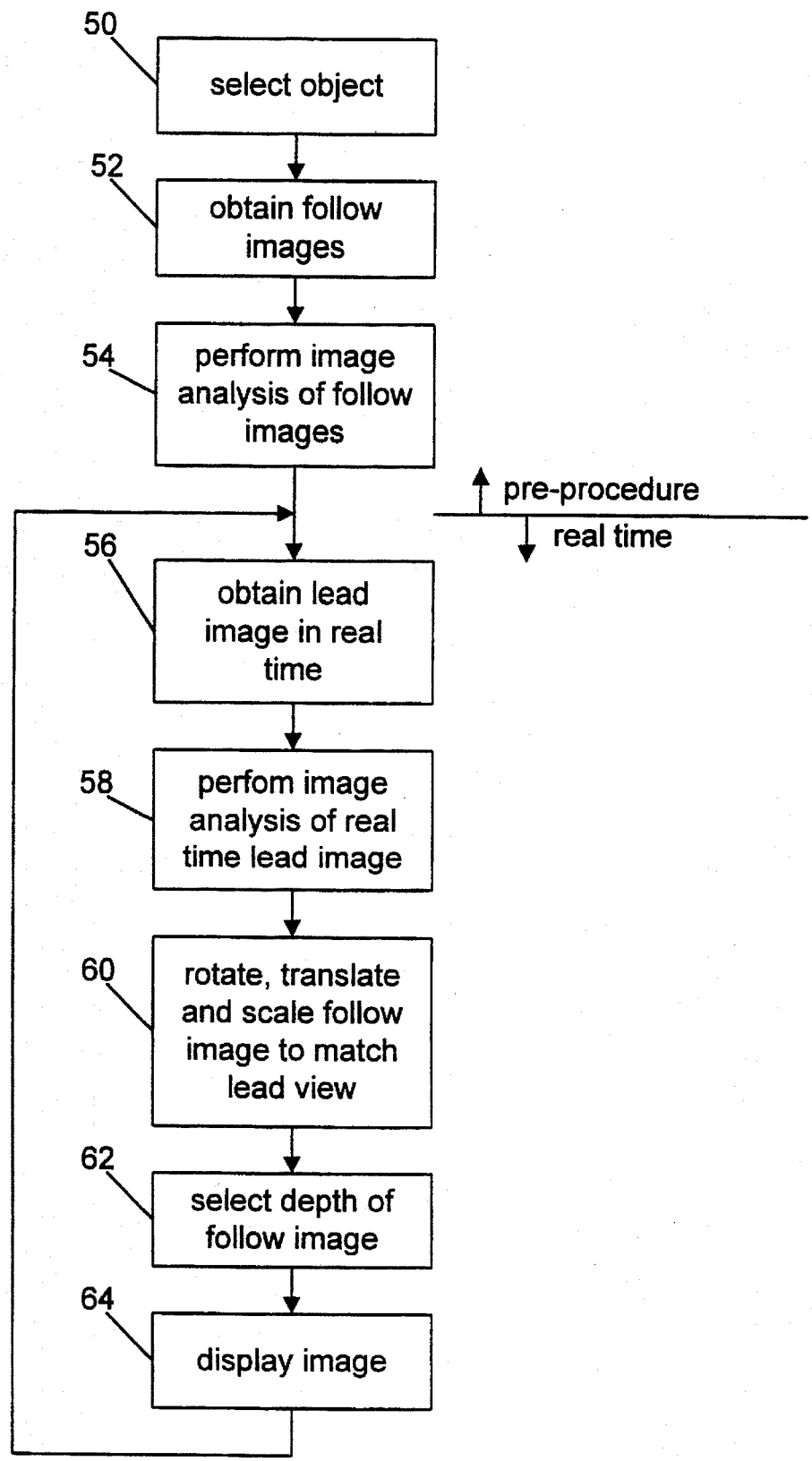
FIG. 3 is a flow chart illustrating an alternative embodiment of the method of this invention.

A second alternative embodiment is shown in FIG. 3. This alternative embodiment omits the steps of obtaining lead images and interreferencing the lead images with the follow images during the pre-procedure part of the method. Rather, the lead image obtained in real time by the lead imager can be interreferenced directly with the follow images without benefit of a preexisting table or map correlating earlier-obtained lead images with follow images by performing the segmentation and classification steps between the lead image and the follow images in real time or by using other image or pattern matching techniques (such as those described in Haralick, R. M., et al., "Computer and Robot Vision," vol. 2, pp. 289–377 (Addison Wesley 1993); Siy, P., et al., "Fuzzy Logic for Handwritten Numeral Character Recognition," in Bezdek, J. C., et al., "Fuzzy Models for Pattern Recognition," pp. 321–325 (IEEE 1992)); Davies, E. R., "Machine Vision: Theory, Algorithms, Practicalities," pp. 345–368 (Academic Press 1992)). This second alternative method increases the real time load on the system processor, which could result in a slower display refresh time, i.e., the time between successively displayed images. The slower display refresh time might be acceptable for certain procedures, however. In addition, one advantage of this approach is that it eliminates some of the time spent in the pre-procedure stage.

In other alternative embodiments, the methods shown in FIGS. 2 and 3 can be practiced using relational data about multiple fiducial markers on the object. For example, instead of determining the orientation of the object by determining the orientation of a single fiducial marker, as in the preferred embodiment, orientation and size information regarding the lead and follow images can be determined via triangulation by determining the relative position of the multiple fiducial markers as seen from a particular line of view. (See "On The Cutting Edge of Technology," pp. pp. 2–14 (Sams Publishing 1993); Moshell, J. M., "A Survey of Virtual Environments," Virtual Reality World Jan/Feb. 1994, pp. 24–36). As another alternative, image analysis techniques can be used to track the movement of the camera or the head rather than its position directly. (See Haralick, R. M., et al., "Computer and Robot Vision," vol. 2, pp. 187–288 (Addison-Wesley 1993); Faugeras, "Three-Dimensional Computer Vision," pp. 245–300 (MIT Press 1989)).

As a further alternative, instead of identifying fiducial markers, pattern matching techniques as described in Davies, Haralick, and Siy may be used for either pre-process or real time matching of corresponding images.

The following is an example of the first preferred embodiment in which the imaging system and method is used to generate and display an image of a patient's head. The two images are: (1) the surgeon's view (produced by a digital video camera mounted on the surgeon's head and pointed at the surface of the patient's head) for the lead image and (2) a three-dimensional CT image of the patient's head as the follow image.

The images are obtained in the pre-procedure stage by a processing computer via a frame-grabber (for the video lead image library) and as a pre-created file including line of view information (for the CT follow image library) and are placed in two separate memory buffers or image libraries. As previously described, the lead images and follow images are preferably obtained while the patient wears a stereotactic head frame. Using the frame's precision instrument guides (preferably, but not necessarily, with a robotic device), numerous video images are taken from a variety of perspectives around the head. Each image is stored in the lead image library along with the line of view, or trajectory, along which that image was obtained. The stereotactic frame is then removed.

The images in the lead image library are interreferenced with images in the follow image library by correlating the lines of view derived in the image obtaining steps. This interreferencing information is used later in the real time portion of the imaging process.

After gathering the pre-procedure lead and follow image information, the imaging system may be used to obtain and display real time images of the patient. In this example, the real time lead image is obtained via a head-mounted video camera that tracks the physician's line of sight. Each real time lead video image is captured by a frame grabber and analyzed to identify predetermined fiducial markers according to the following process.

The real time lead images are segmented via the Canny edge detection technique (Lewis, R. "Practical Digital Image Processing", pp. 211–217 (Ellis Horwood Limited (1990)), which identifies the boundaries between different structures that appear in an image. The fiducial marker for this example is the eye orbit of the patient's skull, which has been enhanced by drawing a circumferential ring with a marker pen. The orbital rims can be seen both on the surface of the face with a video camera as bony ridges. To perform the classification step, the computer might be told, for example, that a left eye orbit is a roughly circular segmented object with a size between 52 and 150 pixels, with a pixel gray value between the threshold numbers of 0 and 75, which occurs on the left side of the video images.

From various angles of view, the orbits appear as ellipses, once they have been segmented. When viewed face-to-face with the patient, the ellipses representing the orbits will, at least when considered as a pair, most closely approximate circles. In mathematical/image analysis terms, that is to say that the major axis (the long axis of an ellipse) is most closely equal to the minor axis (the short axis of an ellipse). As one moves along the x axis, the horizontal axis becomes increasingly shortened, lowering the "axis ratio." At the same time, the "ellipse angle" (the angle in degrees between the major axis and the x axis) is approximately 90°. By contrast, as one moves along the y axis, the axis ratio of the ellipses also decreases accordingly, but the ellipse angle is now approximately 0°.

One can appreciate that any combination between these extremes of pure vertical and pure horizontal viewpoint changes would be accordingly reflected in the axis ratio and ellipse angle measurements. Hence, any given view can be determined, or classified, as being along a certain line of view. Left and right views will not be confused because of the spacial relationship between the two ellipses (one orbit is to the left of the other). In this way, a computer program can be "taught" that an ellipse of given shapes and orientation correspond to the head at a specific orientation. Major and minor axes and their ratio are calculated by well-known formulas (Pratt, W. K., "Digital Image Processing," p. 644, (John Wiley & Sons 1991)), and are a standard feature in commercially available software packages like Global Lab. Such tools also make it possible to analyze images so that they can be "matched" to other images which show the fiducial markers from the same perspective.

After the orbits have been identified, the derived orientation of the real time lead image is compared to the stored information regarding the pre-procedure lead images to identify the pre-procedure lead image that corresponds to the physician's line of view. Because of the earlier interreferencing of the lead and follow images, identification of the lead image line of view will provide the correct follow image line of view. If the real time line of view does not correspond exactly with any of the stored lead image lines of view, the system will interpolate to approximate the correct line of view.

After determination of the correct line of view, the follow image must be translated, rotated and scaled to match the real time image. As with the line of view, these transformation steps are performed by comparing the location, orientation and size of the fiducial marker (in this example, the orbit) of the real time video image with the same parameters of the fiducial marker in the corresponding lead library image, and applying them to the follow image, in combination with a predesignated scaling factor which relates the size of the images in the lead and follow libraries.

After any transformation of the follow image, the follow image must be sliced at the appropriate depth. The depth can be selected by use of an input mechanism associated with the system, such as a mouse, knob, joystick or keyboard. The resulting follow image slice is then displayed on a head-mounted, see-through display worn by the physician, such as the displays marketed by RPI Advanced Technology Group (San Francisco, Calif.) and by Virtual Reality, Inc. (Pleasantville, N.Y.).

The process repeats either on demand or automatically as new real time lead images are obtained by the video camera.

Modifications are possible without departing from the scope of this invention. For example, the imaging modalities could be angiography (done preoperatively) and fluoroscopy (done in real time and used as either a lead or follow image), so that the location of a medical instrument inserted into a patient's body can be tracked in real time.

Furthermore, although the examples described above primarily use single body markers (e.g. eyes, ears) as the key to establishing a line of view, it is anticipated that the simultaneous consideration of many features and the determination of a best match during classification would yield the most accurate results. Generally, the more fiducial markers and features the computer can identify, the more accurate at determining source image orientation the computer will become. Furthermore, by considering more features in the object being recognized, additional source image data can be obtained. For example, the area of the ellipses can be used to correlate the sizes of the two images during the scaling process. Artificial markers, such as foil of various shapes pasted on the skin, clothing, or surgical drapes may also serve the same purpose.

It is possible to use more than two different imaging modalities to prepare a composite image, with one of the images serving as a "linking" image for the purpose of matching fiducial markers in the other two images. For example, the anterior commissure and posterior commissure of the brain might be visible on both MRI and CT. Hence those common points of reference allow two entirely separate image coordinate systems to be related to one another. Hence, the "follow image" could be a composite of data obtained by several modalities, previously registered by established means (Kelly, p. 209–225), or a series of separate follow images sequentially registered to each other, or to the lead image by methods herein described. In this way, a surface video camera could be correlated with the CT via the MR coordinate link.

The instant invention is shown and described herein in what is considered to be the most practical and preferred embodiments. It is recognized, however, that departures can be made therefrom which are within the scope of the invention, and that modifications will occur to those of skill in the art upon reading this disclosure.

All references cited herein are incorporated herein by reference in their entirety.

What is claimed is:

1. A method for obtaining and displaying an image of an object comprising the following steps:

(1) obtaining a follow image library of the object via a first imaging modality;

(2) obtaining a real time lead image of the object via a second imaging modality along a lead view;

(3) referencing the real time lead image to the follow image library via digital image analysis to identify a follow image line of view corresponding to the lead view;

(4) transforming a follow image to correspond to the scale, rotation and position of the real time lead image; and (5) displaying the transformed follow image without displaying the real time lead image, the referencing, transforming and displaying steps being performed substantially in real time after the step of obtaining the real time lead image.

2. The method of claim 1 further comprising slicing the transformed follow image to a selected depth prior to the displaying step.

3. An imaging apparatus comprising:

a follow image library;

a lead imager;

a see-through display; and processing means for interreferencing in real time images from the lead imager with a follow image from the follow image library and for displaying images on the see-through display.

4. The apparatus of claim 3 further comprising a depth controller for selecting a depth at which a follow image should be sliced.

5. The apparatus of claim 3 further comprising a lead image library, the processing means further comprising means for interreferencing in real time images from the lead imager with a lead image from the lead image library.

6. The apparatus of claim 3 wherein the see-through display comprises means for mounting the display on a user's head.

7. A method for obtaining and displaying an image of an object having an exterior surface and an interior, the method comprising the following steps:
   (1) obtaining a follow image library of the object via a first imaging modality;
   (2) obtaining a real time lead image of the exterior surface of the object via a second imaging modality substantially along a user's line of sight to the exterior surface;
   (3) referencing the lead image to the follow image library to identify a follow image line of view corresponding to the line of sight;
   (4) transforming a follow image to correspond to the scale, rotation and position of the real time lead image; and
   (5) displaying the transformed follow image, the referencing, transforming and displaying steps being performed substantially in real time after the step of obtaining the real time lead image.

8. The method of claim 7 wherein the displaying step comprises forming a composite image from the real time lead image and the transformed follow image and displaying the composite image.

9. The method of claim 7 wherein the referencing step comprises segmenting the real time lead image and the follow image into first and second sets of subobjects.

10. The method of claim 9 wherein the identifying step further comprises classifying the subobjects.

11. The method of claim 7 wherein the step of obtaining a follow image library comprises viewing the interior of the object.

12. The method of claim 7 wherein the displaying step comprises the step of displaying the transformed follow image in the user's line of sight to the exterior of the object.

13. The method of claim 7 wherein the displaying step comprises the step of displaying the transformed follow image on a see-through display mounted on the user's head.

14. The method of claim 7 further comprising, prior to the step of obtaining the real time lead image, the steps of
   providing a lead image library, and
   correlating the lead image library to the follow image library.

15. The method of claim 14 wherein a stereotactic frame is used to obtain the follow image library and the lead image library, the step of correlating the lead image library comprising using line of view information provided by the stereotactic frame.

16. The method of claim 14 wherein the step of referencing the real time lead image to the follow image library comprises the use of digital image analysis to correlate the real time lead image with a lead image in the lead image library.

17. The method of claim 14 wherein the step of correlating the lead image library to the follow image library comprises the use of digital image analysis.

18. The method of claim 7 further comprising the step of slicing the transformed follow image to a selected depth prior to the displaying step.

19. A method for obtaining and displaying an image of an object comprising the following steps:
   (1) obtaining a follow image library of the object via a first imaging modality;
   (2) obtaining a lead image library of the object via a second imaging modality;
   (3) correlating the lead image library to the follow image library;
   (4) obtaining a real time lead image of the object along a lead view;
   (5) comparing the real time lead image to the lead library images to identify a lead library image corresponding to the real time lead view;
   (6) transforming the follow image to correspond to the identified lead library image;
   (7) transforming the follow image to correspond to the scale and position represented by the real time lead image; and
   (8) displaying the transformed follow image, the comparing, transforming and displaying steps being performed substantially in real time after the step of obtaining the lead image in real time.

20. The method of claim 19 further comprising slicing the transformed follow image to a selected depth prior to the displaying step.

21. The method of claim 19 wherein the steps of obtaining a follow image library and obtaining a lead image library are performed by maintaining common physical coordinates while obtaining the lead library and follow library images, the step of correlating the lead image library to the follow image library comprising using coordinate information from both libraries.

22. The method of claim 21 wherein the coordinate information is provided by a stereotactic frame.

23. The method of claim 19 wherein the step of correlating the real time lead image to the lead library images comprises the use of digital image analysis.

24. The method of claim 19 wherein the lead view comprises a user's line of sight.

25. The method of claim 19 wherein the step of obtaining a follow image library comprises obtaining a follow image library of the object's interior, the step of obtaining a lead image library comprises obtaining a lead image library of the object's exterior substantially along a user's line of sight to the object, and the step of obtaining a real time lead image comprises obtaining a real time lead image of the object's exterior.

26. The method of claim 25 wherein displaying step comprises the step of the displaying the transformed follow image along the user's line of sight to the exterior of the object.

27. The method of claim 19 wherein the displaying step comprises the step of displaying the transformed follow image on a see-through display mounted on the user's head.

28. The method of claim 19 wherein the step of correlating the lead image library to the follow image library comprises using digital image analysis.

29. The method of claim 19 wherein the second imaging modality is video imaging.

30. A method for obtaining and displaying an image of an object having an exterior surface and an interior, the method comprising the following steps:
   (1) obtaining a follow image library of the object via a first imaging modality;

(2) obtaining a real time lead image of the exterior surface of the object substantially along a user's line of sight to the exterior surface;

(3) referencing the real time lead image to the follow image library to identify a follow image line to select a follow image corresponding to the scale, rotation and position of the real time lead image; and (4) displaying the selected follow image, the referencing and displaying steps being performed substantially in real time after the step of obtaining the real time lead image.

31. An imaging apparatus comprising:

a follow image library;

a lead imager comprising a camera mounted on a user's head;

processing means for interreferencing in real time images from the lead imager with the follow image library; and means for displaying a follow image from the follow image library.

32. The apparatus of claim 31 further comprising a lead image library, the processing means comprising means for correlating the lead image library to the follow image library.

* * * * *